United States Patent
Solomon et al.

(10) Patent No.: US 7,329,418 B2
(45) Date of Patent: *Feb. 12, 2008

(54) PHARMACEUTICAL TABLETS HAVING HEIGHT GREATER THAN WIDTH

(75) Inventors: Lawrence Solomon, Boca Raton, FL (US); Allan S. Kaplan, Boca Raton, FL (US)

(73) Assignee: Accu Break Technologies, Inc., Plantation, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/678,408

(22) Filed: Feb. 23, 2007

(65) Prior Publication Data
US 2007/0141155 A1    Jun. 21, 2007

Related U.S. Application Data

(63) Continuation-in-part of application No. 11/569,343, filed on Nov. 17, 2006, and a continuation-in-part of application No. 10/598,306, filed on Aug. 24, 2006, and a continuation-in-part of application No. 10/598,267, filed on Aug. 23, 2006.

(51) Int. Cl.
*A61K 9/20*  (2006.01)
*A61K 9/44*  (2006.01)
*A61K 9/22*  (2006.01)
*A61K 9/24*  (2006.01)

(52) U.S. Cl. .................... 424/464; 424/465; 424/467; 424/472; 424/473; 424/468

(58) Field of Classification Search .................... None
See application file for complete search history.

(56) References Cited

U.S. PATENT DOCUMENTS

| | | | |
|---|---|---|---|
| 3,128,226 A | | 4/1964 | Rubin et al. |
| 5,478,901 A | * | 12/1995 | Jones et al. .................. 526/170 |
| 5,626,874 A | | 5/1997 | Conte et al. |
| 5,681,583 A | | 10/1997 | Conte et al. |
| 5,817,340 A | | 10/1998 | Roche et al. |
| 6,086,919 A | | 7/2000 | Bauer et al. |
| 6,161,260 A | * | 12/2000 | Flewitt ....................... D24/101 |
| 6,183,778 B1 | | 2/2001 | Conte et al. |

(Continued)

OTHER PUBLICATIONS

H.A. Lieberman and L. Lachman, Pharmaceutical Dosage Forms, vol. 1, pp. 217-223, Marcel Dekker, Inc., New York, New York.

*Primary Examiner*—Lakshmi S. Channavajjala
(74) *Attorney, Agent, or Firm*—Ted W. Whitlock

(57) ABSTRACT

An immediate release compressed pharmaceutical tablet that has two or more segments and a top and a bottom and has a height that exceeds the width of the tablet. The height is measured vertically from the top to the bottom of the tablet while it is in the tablet die in which it is fully compressed, after compression has been completed. The width is measured as the greatest horizontal dimension of the tablet at a location halfway between the top and the bottom of the tablet, except that when the horizontal cross-section of the tablet is substantially rectangular, the width is defined by locating the two shorter sides of the perimeter of the horizontal cross-section, and measuring the length of a line that is at right angle to the shorter sides.

20 Claims, 3 Drawing Sheets

U.S. PATENT DOCUMENTS

| | | |
|---|---|---|
| 6,294,200 B1 | 9/2001 | Conte et al. |
| 6,309,668 B1 | 10/2001 | Bastin et al. |
| 6,919,373 B1 | 7/2005 | Lam et al. |
| 7,011,849 B2 | 3/2006 | Storm et al. |
| 2002/0132850 A1 | 9/2002 | Bartholomaus |
| 2005/0013863 A1* | 1/2005 | Lim et al. .................. 424/472 |
| 2005/0038039 A1 | 2/2005 | Fanara et al. |
| 2006/0280794 A1 | 12/2006 | Hamaguchi et al. |

* cited by examiner

PHARMACEUTICAL TABLETS HAVING HEIGHT GREATER THAN WIDTH

CROSS-REFERENCE TO RELATED APPLICATIONS

This is a continuation-in-part of pending U.S. patent application Ser. No. 11/569,343 filed Nov. 17, 2006 pursuant to 35 USC 371 as a national stage application from PCT/US05/18633 filed May 23, 2005 which claims priority to U.S. Provisional Appl'n Ser. No. 60/573,042 filed May 21, 2004 and U.S. Provisional Appl'n Ser. No. 60/573,134 filed May 21, 2004.

This is also a continuation-in-part of pending U.S. patent application Ser. No. 10/598,267 filed Aug. 23, 2006 pursuant to 35 USC 371 as a national stage application from PCT/US05/18638 filed May 23, 2005 which claims priority to U.S. Provisional Appl'n Ser. No. 60/573,042 filed May 21, 2004 and U.S. Provisional Appl'n Ser. No. 60/573,134 filed May 21, 2004.

This is also a continuation-in-part of pending U.S. patent application Ser. No. 10/598,306 filed Aug. 24, 2006 pursuant to 35 USC 371 as a national stage application from PCT/US05/18639 filed May 23, 2005 which claims priority to U.S. Provisional Appl'n Ser. No. 60/573,042 filed May 21, 2004 and U.S. Provisional Appl'n Ser. No. 60/573,134 filed May 21, 2004.

Each of the above patent applications is hereby incorporated by reference in its entirety, as applicable.

FIELD OF THE INVENTION

The invention provides immediate release, segmented and non-homogeneous compressed pharmaceutical tablets that are taller than they are wide. This novel configuration for immediate release tablets can result in previously undisclosed advantages with so that breaking of the tablet may more easily produce predictable, accurate quantities of active ingredient(s). The subject invention further relates to layered and segmented pharmaceutical tablets that include a segment comprising a relatively inactive composition. Tablets of the invention are also preferably scored in a novel manner.

BACKGROUND

Pharmaceutical tablets in divisible form containing an indentation known as a score have long been known and widely used. Problems with breaking scored tablets are well-known. These problems include loss of active drug and inaccurate division of the tablet, so that a tablet intended to be divided into two equal half-tablets often does not come close to that ideal.

Many drugs, such as warfarin, require dosage adjustments and are frequently broken. These dosage adjustments through tablet breaking by patients have been determined to be imprecise. As the following discussion demonstrates, for many years experts have called upon the pharmaceutical industry to improve the quality of tablet breaking, but limited attention has previously been paid to these calls by the pharmaceutical industry.

In 1984, Stimpel et al. ("Stimpel"), described the relative accuracy of breaking of various tablets for treatment of cardiovascular problems. M. Stimpel et al., "Breaking Tablets in Half." *The Lancet* (1984):1299. Even though breaking was performed by a sophisticated, dexterous person, Stimpel found that breaking was not accurate, and opined that real world use by patients would provide yet more unsatisfactory results. Stimpel called upon the pharmaceutical industry to improve the accuracy of splitting tablets: "Clearly any assumption that halving a tablet will not lead to inaccurate doses is invalid. This potential source of inaccuracy could be even more significant in clinical situations (our study was done under ideal conditions) and the pharmaceutical industry should tackle it, either by improving divisibility (as already has been done for lopressor and logroton) or, even better, by marketing a wider range of unscored tablets to provide all the doses that might be indicated clinically."

Despite that finding and statement, and despite the subsequent issuance of various patents relating to optimizing a scoring pattern and/or tablet shape, Rodenhuis et al., (2004) noted that: "Improving the functioning of score lines may be a more practical approach than banning this dosage form" (emphasis added). N. Rodenhuis et al., "The rationale of scored tablets as dosage form." *European J. of Pharmaceutical Sciences* 21 (2004):305-308 (hereafter "Rodenhuis"). Rodenhuis observed that European regulatory authorities started a policy to discourage scoring of tablets in 1998. This policy change, according to Rodenhuis, likely related to "many recent reports of bad functioning score lines" that "many scored tablets are difficult to break," and that "many scored tablets show unsatisfactory mass uniformity of the subdivided halves." The authors then go on to describe useful aspects of scoring tablets. For a comprehensive review article on this topic, see van Santen, E., Barends, D. M. and Frijlink, H. W. "Breaking of scored tablets: a review" *European J. of Pharmaceutics and Biopharmaceutics* 53 (2002):139-145.

Some current studies that demonstrate the severity of the problem are described below. Peek et al., (2002), studied tablet splitting by "elderly patients" aged 50-79. Peek, B. T., Al-Achi, A., and Coombs, S. J. "Accuracy of Tablet Splitting by Elderly Patients," *The Journal of the American Medical Association* 288 No.4 (2002):139-145. Breaking scored tablets with mechanical tablet splitters without specific instruction led to highly unsatisfactory separating of the tablets. For example, warfarin 5 mg was on average split into 1.9 and 3.1 mg tablets. This potent anticoagulant has such a narrow therapeutic range that 2, 2.5, and 3 mg tablet doses are manufactured. Biron et al., (1999), demonstrated that warfarin 10 mg also often split to less than 4.25 or greater than 5.75 mg. Biron, C., Liczner, P., Hansel, S. and Schved, J. F., "Oral Anticoagulant Drugs: Do Not Cut Tablets in Quarters." *Thromb Haemost* 1201 (1999). In addition, they demonstrated that loss of mass due to crumbling or chipping from the breaking of the warfarin tablets was statistically significant. They also demonstrated that quartering of the tablets was grossly inaccurate.

McDevitt et al., (1998), found that 25 mg scored hydrochlorothiazide tablets were manually split badly enough that 12.4% deviated by more than 20% from ideal weight. McDevitt, J. T., Gurst, A. H. and Chen, Y. "Accuracy of Tablet Splitting." *Pharmacotherapy* 18 No.1 (1998):193-197. 77% of the test subjects stated that they would be willing to pay a premium for individually produced 12.5 mg tablets rather than split 25 mg unscored tablets.

Rosenberg et al., (2002), studied pharmacist-dispensed split tablets. Rosenberg, J. M., Nathan, J. P. and Plakogiannis, F. "Weight Variability of Pharmacist-Dispensed Split Tablets." *Journal of American Pharmaceutical Association* 42 No.2 (2002):200-205. They found that "tablet splitting resulted in an unacceptably high incidence of weight variation." They recommended that "standards should be developed to ensure uniformity of split tablets."

Teng et al., (2002), using a trained individual in a laboratory setting to split tablets, concluded that "the majority of the 11 drug products we tested, when assessed for their ability to be split into half-tablets of equal dose, failed a liberally interpreted USP (United States Pharmacopeia) uniformity test . . . The practice of dividing tablets to save costs or to improve a dosage regimen . . . is not recommended for patients using drugs with more substantial toxicity and steep dose-response efficacy curves." Teng, J., Song, C. K., Williams, R. L. and Polli, J. E. "Lack of Medication Dose Uniformity in Commonly Split Tablets." *Journal of American Pharmaceutical Association* 42 No. 2 (2002):195-199.

Rodenhuis reported that 31% of all tablets in one Netherlands study were subdivided before being swallowed. In the U.S., "managed care" insurance organizations, the Veterans Administration and others may encourage splitting by patients of unscored tablets that may not even have symmetrical shapes. Many drug products in the US either are unscored tablets, or are provided as capsules despite being able to be produced as tablets.

The invention is directed to amelioration of the problems described above. The subject invention may allow either a single agent or a mixture of two active agents (i.e., one or more drugs) to be accurately divided in halves with regard to the dose, even if the tablet does not break into equal halves by mass.

The current invention describes a tablet shape adapted for separating one vertically disposed segment from another.

In the large field of immediate release pharmaceuticals, the relative dimensions of the tablets in accordance with the subject invention are novel as applied to immediate release dosage forms. Commercially, the only product that as produced is taller than it is wide is Concerta®, which is a three-segment tablet, two of which segments are devoted to controlled release of the active drug, methylphenidate. Concerta utilizes the OROS® system, which utilizes the taller-than-wide geometry to provide a layered tablet configuration to impart controlled release characteristics. The manufacturer's directions for the use of Concerta specify that the tablets should never be broken. Except for Concerta, tablets, including those involving layers vertically disposed one on the other, have been produced wider than they are tall.

A tablet press manufacturer, Korsch AG of Germany, has developed a tablet press (the TRP 900) that can produce up to five vertically disposed layers. It has been utilized to produce taller-than-wide five-layer tablets having no active drugs therein and has also been used to manufacture Concerta.

SUMMARY OF THE INVENTION

The invention is directed to an immediate release compressed pharmaceutical tablet that has two or more segments, has a top and a bottom, and has a height that exceeds the width of said tablet, said height being measured vertically from the top to the bottom of said tablet while it is in the tablet die in which it is fully compressed, after said compression has been completed; and said width being measured as the greatest horizontal dimension of the tablet at a location halfway between said top and said bottom of said tablet, except that when the horizontal cross-section of said tablet is substantially rectangular, the width is defined by locating the two shorter sides of the perimeter of said horizontal cross-section, and measuring the length of a line that is at right angle to said shorter sides. The height, width and any other dimensions or orientations or terms relating to tablet dimensions and structure such as "transverse" and "tallness" relate to the position of the tablet in the die after final compression but before removal or ejection from the die. Where the tablet has "cupping" of the top and/or bottom surfaces, the height relates to the maximal vertical distance, which will generally occur in the middle of the top surface as if there were a plumb line vertically dropped to the middle of the bottom surface.

A preferred embodiment of the invention is an immediate release compressed pharmaceutical tablet that comprises three or more discrete segments disposed one above the other. The invention contemplates immediate release pharmaceutical tablets, preferably containing a pharmacologically effective quantity of a drug, where the height of the tablet (vertical dimension) exceeds its width (horizontally dimension); i.e., the tablet is taller than it is wide. The terms "vertical" and "horizontal" ("horizontal" is also referred to as "transverse") axis of the tablets of the invention are determined by and have the same orientation as that of the tablet die in which the tablet is compressed in a tablet press or other tabletting machine ("tablet press" herein), and the order of entry of granulations into the die.

Tablets of the invention are most preferably produced for commercial sale in a high-speed tabletting machine. Tablets are produced in a die of said tabletting machine. In such a machine, granulations enter the tablet die one on top of another so that said granulations are said to be vertically disposed to each other. Layers and segments formed from vertically disposed granulations are considered to be vertically disposed, as well. The height ("tallness") of a tablet is measured as the vertical distance between the lowest part of the first granulation to enter the die to the highest part of the last granulation to enter the die (said first granulation forms the bottom layer and said last granulation forms the top layer).

The width is a horizontal (transverse) dimension. In determining the width, diagonal measurements are not taken through the horizontal aspect of the tablet if the tablet is substantially rectangular in transverse cross-section: If the perimeter of the horizontal aspect of the tablet were rectangular (and not square), then the width of the tablet would be the greater of the two perimeter measurements as is typically used to describe a rectangle, and not the diagonal that is calculated by the Pythagorean theorem and that uses said perimeter measurements to calculate said diagonal. Similarly, tablets with a substantially rectangular vertical cross-sectional configuration have a height that is measured as a perimeter and not a diagonal measurement. When a vertical or horizontal cross-sectional configuration is not substantially rectangular, which includes triangles, rhombi, and hexagons, the greatest dimension through said cross-section represents said height or width.

Preferred tablets of the invention utilize segments that lack a pharmacologically effective dose of a drug, providing a discrete breaking unit that can serve as an inactive region or area for breaking through the tablet without breaking any substantial portion of an active segment, thereby providing an accurate partial dose of drug contained in the whole tablet, as desired.

By convention herein, the term "contains a drug," when used to refer to a granulation, layer, or segment of a tablet, said granulation, layer or segment, or a plurality thereof, has within it a pharmacologically effective dose of an active pharmaceutical ingredient, or drug. The term "contain a drug or drugs" when used to refer to a granulation, layer, or segment means that said granulation, layer or segment, or a plurality thereof, may contain either a single drug or a specific ratio of a plurality of drugs.

A layer or segment, but not a granulation, is said to "lack a drug (or drugs)" or to be "substantially free of a drug or drugs" or is an "inactive" layer or segment if said layer or segment is formed from a composition that either contains none (or an undetectable amount) of said drug or drugs, or contains a pharmacologically ineffective amount of said drug or drugs, by design or as a result of inadvertent intermixing during manufacture. For example, a composition containing only pharmaceutical excipients and no drug that, by being formed into a layer or segment, then contains small amounts of drug resulting from intermixing or carry-over from an adjacent active drug-containing composition, is considered to be substantially free of drug and an "inactive" layer or segment for purposes of the subject invention. Parts of speech, such as "contain," "contains," "containing," and "lacking" in relation to the above two paragraphs also are terms of art with otherwise the same meanings to those described therein.

In preferred embodiments, but without limitation, the invention comprises compressed immediate release pharmaceutical tablets where one or more drugs are disposed in segments where: (a) said tablet includes two or more segments that contain the same drug or drugs in the same or different concentrations relative to the excipients found in said segments, and the tablet is not provided with another drug than is found in said segments; or (b) said tablet includes a first segment containing a drug or drugs; a second segment; and a third segment containing the same drug as the drug in said first segment, said second segment being interposed between said first and said third segment, and said second segment lacking said drug or drugs.

In a more preferred embodiment, the tablets of the invention have at least two compositionally distinct segments, with a first segment containing an active drug or drugs in a pharmacologically effective amount and a second segment that:

(a) contains the same drug at a lower concentration than the concentration of said drug in said first segment, or contains the same ratio of the drugs in said segment; or (b) lacks said drug or drugs present in said first segment and the tablet also has a third segment containing the same drug that is present in said first segment.

A most preferred embodiment of the subject invention concerns a compressed, immediate-release pharmaceutical tablet containing a therapeutic dose of one or more active pharmaceutical ingredients and having a greater height than width, said height being measured vertically from the top to the bottom of said tablet while it is in the tablet die in which it is fully compressed, after said compression has been completed; and said width being measured as the greatest horizontal dimension of the tablet at a location halfway between said top and said bottom of said tablet, except that when the horizontal cross-section of said tablet is substantially rectangular, the width is defined by locating the two shorter sides of the perimeter of said horizontal cross-section, and measuring the length of a line that is at right angle to said shorter sides, said tablet consisting essentially of:

a bottom end segment comprising an immediate-release composition containing at least about half of said therapeutic dose of the one or more active pharmaceutical ingredient, said bottom end segment having an exposed bottom end and a contacting face opposite its exposed bottom end;

a top end segment comprising a composition substantially identical to the composition of said bottom end segment, said top end segment having an exposed top end and a contacting face opposite its exposed top end;

a middle segment located between said bottom end segment and said top end segment, said middle segment comprising a composition consisting essentially of immediate-release excipients and being substantially free of active pharmaceutical ingredient, said middle segment having a bottom face in contact with the contacting face of said bottom end segment, a top face in contact with the contacting face of said top end segment, and an exposed outer side surface; and, optionally, an immediate-release coating substantially free of active pharmaceutical ingredient.

The coating composition preferably comprises pharmaceutically acceptable ingredients that, when applied to the outside of the tablet, has substantially no effect on release kinetics of active drug from the tablet or tablette. In one preferred embodiment, the coating composition is a water-soluble composition comprising a sugar or starch (e.g., a saccharose), or a water-soluble polymeric composition (e.g., a low molecular weight hydoxypropyl methylcellulose or polyvinylpyrrolidone) or comprises other pharmaceutically acceptable excipients that are conventionally used as coatings for immediate-release tablets.

Thus, a preferred tablet of the subject invention comprises two identical active compositions layered to form discrete segments at each end of a taller-than-wide tablet. An inactive composition forms a third, discrete middle layer or segment and is positioned between those active end segments (i.e., above the bottom end segment and below the top end segment in the tablet die). The inactive middle segment can therefore serve as a discrete breaking unit or region or segment, providing an advantage of allowing a person to easily and accurately separate the end segments from one another, thereby dividing the close contained within the whole tablet, without breaking any substantial part of, or losing any substantial amount of active ingredient from, either end segment. This advantage can ensure that the amount of drug contained within each active end segment in the whole tablet is substantially the same even after the tablet is broken into tablettes.

A tablet of the subject invention can further contain guides for tablet breaking, such as a score, or a other separation marks or indicia, such as printed indicia, or a perforation, on or in the side of the tablet. The score or other marking is preferably oriented substantially horizontally in relation to the vertical axis of the tablet to provide a guide to or assist in allowing tablet breaking only through one segment, e.g., only through the inactive middle segment. A side of a tablet is an external part of said tablet that has a vertical part that is substantially parallel to the theoretical vertical axis of the tablet; a side is in contact with the inner wall or face of the tablet die in which said tablet is compressed. A preferred tablet includes a score oriented horizontally in reference to the longitudinal or vertical axis (height) of the tablet, and which is placed in the middle inactive segment. Accordingly, in a preferred embodiment of the compressed, immediate release tablet described above, the middle segment comprises a substantially horizontal score positioned such that a plane passing through said score substantially bisects the tablet or middle segment. In addition, or in an alternative preferred embodiment of the compressed, immediate release tablet of the subject invention, the middle segment can comprise printed indicia forming a mark or guide or the like to indicate or suggest a breaking region or area, the printed indicia being preferably formed as a line or other like marking oriented substantially horizontally on all exposed side of the middle segment such that a plane passing through said printed indicia substantially bisects the tablet or middle segment. It would be understood that a tablet of the subject invention may include a score and printed indicia on the same or on different segments.

The compressed pharmaceutical tablets can include one or more active pharmaceutical ingredient (API) suitable for preparation into a compressible composition or formulated with a pharmaceutically acceptable carrier or carriers such that the formulation can be compressed into tablet form. Preferably, the API is a drug that is approved or is approvable for commercial sale in the United States, such as warfarin, a statin, risperidone, methotrexate, metformin, atenolol, prednisone, phenytoin, lamotrigine, or meloxicam.

Taller-than-wide tablets of the invention are shaped to be more easily broken through the tablet's theoretical vertical axis (i.e., in a horizontal direction) than conventional, currently-manufactured tablets having a "wider than tall" configuration. Many preferred uses of tablets of the invention are to break through a middle, substantially inactive segment of the tablet without breaking through any segment above or below said middle segment.

It is a primary object of the invention to provide an immediate release pharmaceutical tablet that may be easily broken to provide a partial dose of a drug or drugs that is contained in said tablet.

It is also an object of the invention to provide an immediate release pharmaceutical tablet having three segments, one of which is an interposed segment which is adapted to be broken through in such a manner as to keep the segments between which it is interposed and that contain pharmacologically effective quantities of a drug or drugs substantially intact if said tablet is broken through said interposed segment.

These and other objects of the invention will become apparent from the present application.

DETAILED DESCRIPTION OF THE INVENTION

Figure 1B:
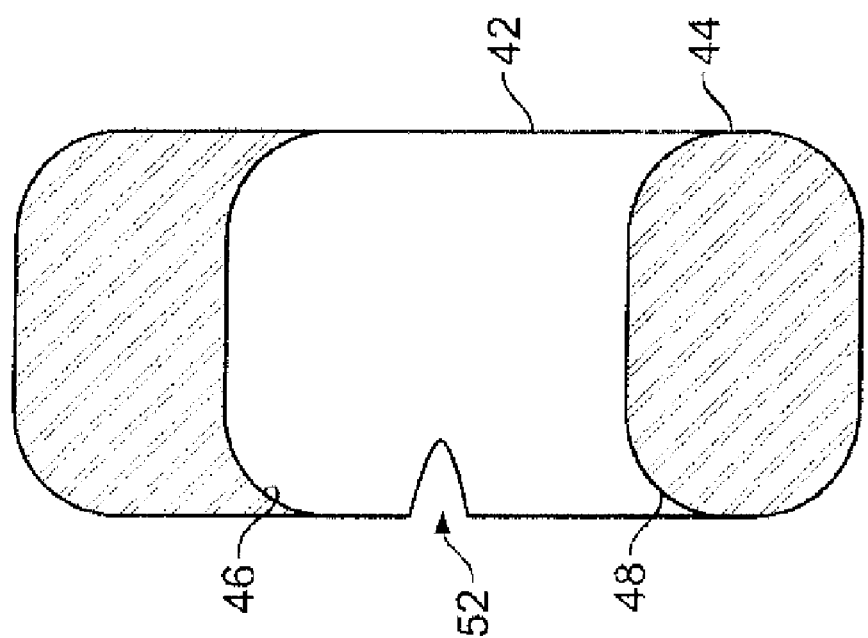
FIG. 1b is a cross-sectional view of the tablet of FIG. 1a looking at the side of the tablet where the score ends.

Tablets of the invention are preferably those compressed in a tablet press. For commercial use, a high-speed three (3)- or five (5)-station press produced by Korsch AG (such as the TRP 700/900 tablet presses) may he utilized. Remington's Pharmaceutical Sciences 20th Ed., Mack Publishing Co., Easton, Pa. (2000), Chapter 45, which is incorporated by reference, describes the various techniques utilized in making compressed tablets, and pharmaceutically acceptable excipients that can be used in a formulation with active pharmaceutical ingredients to form immediate-release compressed tablets of the subject invention. The tablets of the invention are primarily intended for oral administration but they may also be used for other applications. Tablets of the invention are preferably not formed using an adhesive substance, such as cement, glue, other adhesive, or the like to adjoin segments or discrete units.

If an optional coating is provided on the tablets of the invention, such coating preferably comprises a water-soluble coating, e.g., a water-soluble polymeric coating comprising, for example, a water soluble cellulosic polymer, polyvinylpyrrolidone (PVP), or the like, for the well known purposes of aiding in manufacture or handling of the tablet (e.g., to decrease susceptibility to chipping during manufacture or shipping, to improve aesthetics of the tablet, to protect against exposure to light, to improve mouth-feel or to facilitate swallowing of the tablet). A coating provided on an immediate-release tablet of the subject invention preferably does not affect the immediate-release characteristics of the tablet, and preferably is substantially free of active pharmaceutical ingredient. Such coating in accordance with the subject invention is not for the purpose of altering the release kinetics of any active ingredient present in the tablet, such as a swellable or erodible coating used to slow the release of drug from a tablet after ingestion. The coating may contain a color or coloring agent.

The tablets of the invention comprise at least two compositionally different segments, e.g., one active composition disposed to form two different (top and bottom) segments, and one inactive composition disposed to form the middle segment. Thus, two different compositions are used and form three discrete segments in a tablet of the subject invention.

A segment represents the entirety of a contiguous, substantially homogeneous part of a tablet or tablette (see below) of the invention. If two or more consecutive granulations entering the die are substantially identical, then when compressed, they will form one segment. Such a segment is a sub-type of segment that nay be referred to specifically as a compound segment. If, however, two substantially non-identical granulations (such as those containing different active drugs, the same active drugs in different ratios, different excipients or different ratios of similar excipients, or different salts of the same active drug) were compressed onto each other, they would comprise two segments. Granulations comprising the same active drug in the same concentration relative to excipients but with dissimilar excipients would comprise two segments if one granulation were compressed onto another.

A layer is produced by introducing an amount of an individual granulation into a tablet die to fill at least a part of the die. A layer is considered to be present whether it is the form of an un-tamped, tamped or fully compressed granulation.

In many of the most preferred tablets of the invention, a layer, (and the granulation from which it is derived), will not need to be placed on top of or below (e.g., adjoining, or contiguous with) a substantially identical layer (or granulation). In such a case, one layer will give rise to the sub-type of segment that is a simple segment. The use of the term "segment" allows a segment to be simple or compound.

Because the tablets of the invention have been adapted to be broken if and when desired, it has proven useful to develop a term for the major fragments of said breaking. The inventors use the term "tablette" in this regard. An example of tablette formation is as follows. A standard single-scored, mono-layer, homogeneous pharmaceutical tablet is broken. Said breaking produces two major fragments, each of which is called a tablette, generally plus some chips and crumbling which are preferably minor in amount. In the segmented, layered tablets of the invention, to utilize the invention properly may make it advantageous to place a score transversely into a segment, such as all inner segment, as may be done with an instrument such as a file. Successfully breaking said tablet through said score will result in two tablettes, representing the two major fragments of the tablet and not including smaller fragments such as crumbs or chips. The accompanying diagrams help clarify the relationship of tablets to tablettes.

The terms "active agent," "drug," "active drug," "active pharmaceutical agent," "pharmacologically active agent" are interchangeable and include, without limitation, prescription and non-prescription pharmaceutical compounds, as well as pharmacologically effective doses of vitamins, cofactors, and the like. Substances such as foodstuffs, vitamins in "recommended daily allow" quantities, and the like are not considered to be "drugs" herein.

The term "undetectable amount" means that using conventional analytical techniques such as high performance liquid chromatography (HPLC), nuclear magnetic resonance imaging (NMRI), and the like, the presence of an active compound can not be identified. The term "pharmacologically ineffective amount" means an amount of a drug or drugs having no measurable pharmacological effect. Due to the conditions under which high speed automated tabletting equipment are operated, mixing of different granulations may occur during tablet formation which may cause material such as drug substance present in one granulation to appear in a layer or segment where it was not intended to be placed.

The terms "inactive segment" or "substantially inactive segment" or "relatively inactive segment" refers to a segment that either contains an undetectable amount of any drug or contains a diminished concentration of any pharmacologically effective drug or drugs contained in another segment or segments or is formed from a composition that is substantially free of active drug in its manufacture prior to its incorporation into a tablet of the subject invention.

The term "immediate-release" refers to the release of drug from a composition, where the drug is substantially completely released within a time period of about 1 hour or less and, preferably, about 30 minutes or less. An immediate-release dose of drug applied as a coating on the surface of a dosage form, as used herein, refers to a dose of a drug prepared in a suitable pharmaceutically acceptable carrier to form a coating solution that will dissolve rapidly upon administration to thereby provide an immediate-release dose of drug. As is known in the art, such immediate-release drug overcoats may contain the same or a different drug or drugs as is contained within the underlying dosage form.

As used herein, such terms as "horizontal" ("transverse") and "vertical" when used in relation to a tablet, are based on the spatial orientation of the tablet as, and after, it is produced in a die, but before it is removed or ejected from the die. Thus, the top layer (segment) of the tablet is considered to be above the inner and bottom layers (segments). The layers and segments of the tablet are considered to be vertically disposed with regard to each other, as granulations enter and form layers vertically. An "inner" segment is a "middle segment" and the terms are used interchangeably herein.

The height of a tablet represents the vertical distance from the lowest part of the tablet to the level of the highest part. There are two transverse dimensions, measured by taking a cross-section of the tablet through its widest part. Unless the cross-sectional configuration of the tablet is circular or square (excluding beveling or cupping at the periphery of an otherwise square cross-sectional shape), then there are at least two different transverse dimensions. The greater of said two transverse dimensions is called the width, and the lesser is called the depth. Tablets of the invention comprise at least two segments, have release characteristics that are immediate release (i.e., there are no controlled-release or "drug delivery" coatings, additives, or characteristics), and have a height that exceed the width.

As an example of a preferred method of manufacture of a tablet in accordance with the subject invention, first, a granulation containing a pharmacologically effective dose of a drug enters the die and is, optionally, tamped. Second, a granulation lacking a drug (an "inactive granulation") enters the die and is optionally tamped. Optionally, a second and perhaps a third identical granulation lacking active drug also enters the die and is tamped. The inactive granulation(s) create(s) a breaking region or area within the tablet—a part of the tablet that can be identified and broken through so that a part of the tablet containing a significant concentration of drug is not broken through. Last, a second granulation containing a pharmacologically effective quantity of a drug enters the die, is optionally tamped, and then final compression to form a compressed tablet occurs. In the preferred embodiment of the invention, this second granulation is compositionally substantially identical to the first active granulation. While one or all segments may individually have a width greater than height, the tablet as a whole preferably has a height that exceeds its width.

Often, to aid identification of the inactive segment, the top and bottom segments can be of a different color than the middle inactive segment; this is a preferred embodiment. Other markings in or on the tablet may also aid identification; or, it may be advantageous not to make such identification of the different segments obvious.

Subsequent to tablet formation, optionally a score may be placed in the side of said tablet, preferably transversely. Alternatively, after tablet formation, a printed line or other forms of indicia such as dotted lines, symbols or perforations may be placed on or in the surface of the tablet, all of which serve the purpose of allowing identification of said tablet's desired breaking region from the standpoint of effecting accurate separation of the parts of a tablet containing isolated doses of drug.

A horizontal score as described herein for tablets of the subject invention cannot be produced by conventional or commercial tablet manufacturing techniques because to do so would require a corresponding horizontal "shelf" or "embossing" in the die that would allow tablet formation but would prevent ejection of the formed tablet from the die. Such a score may, however, be produced by other means, such as by use of a file manually or by a high-speed manufacturing process. Various methods of applying indicia such as pharmaceutically acceptable inks and banding materials are well known and may be applied to the side of the tablet, such as to locate a region of potentially desired tablet breaking, such as through a relatively inactive middle segment which is interposed (i.e., located) between two segments.

The depth of a score may be from about 0.5 mm to about 3 mm but, preferably, should not exceed from about 40-50% of the thickness (or width) of the tablet. The score can include interrupted, incomplete, or non-contiguous scoring marks. The length of the printed indicia mark is not limited and in the case of a rounded tablet may include 30° to 180° of arc or more preferably from 60 to 120° of arc; in the case of a rectangular, trapezoidal etc. tablet, the score may include from about 10% to 50% percent of the perimeter of the tablet measured at the point where the printed indicia mark is placed.

A score also may be provided within a top segment or a bottom segment, oriented horizontally or vertically, in the tablets of the invention.

Suitable dimensions for tablets according to the invention are; height: 6 to 24 mm; preferably 10 to 18 mm and more preferably from 10 to 14 mm; width (at the widest dimension of the horizontal axis): 2 to 16 mm; preferably 3 to 10 mm and more preferably 4 to 8 mm. Without limitation, the dimensions of the tablet may be optimal if the ratio of the height to the width is between about 1.5:1 to about 3:1. None of these dimensions are limiting, and they are presented regarding use in adult humans. The invention may be useful in animals of different size, in which case preferred dimensions may be very different from those provided immediately above, but could be adjusted or modified by a person of ordinary skill in the art guided by or using the disclosure herein.

Numerous other tablet structures may be created, some of which are further delineated below. Various advantages in the treatment of human patients and other animals in need are created by tablets of the shape described.

Tablets of the invention are most preferably formed in a high-speed tablet press. In a typical manufacturing procedure, two or more different granulations are separately fed into a die, utilizing different filling stations. Wet granulations are often preferred to limit transfer of material from one granulation to another. Direct compression of powder is also a preferred manufacturing technique.

Benefits of the invention include the utilization preferably of inactive granulations, and less preferably, segments with diminished concentration of a drug relative to another segment. Optimally but not necessarily the tablet is provided with a means of identifying an optimal breaking region and of identifying one tablette from another after tablet breaking, an important benefit if the tablettes contain different types or quantities of a drug or drugs.

Because of the novelty of the tablets, it is necessary to describe the top, bottom, sides, etc. of the tablet. It has been found best to describe the tablet with regard to such terms based on said tablet's formation and location in the die in which said tablet is formed.

The bottom segment of a tablet contains the first granulation into the die. The top segment of a tablet contains the last granulation to enter the die. A "side" of the tablet refers to that external part of said tablet in contact with the internal vertical face or aspect of the tablet die in which said tablet is produced. Typically, sides of the tablets of the invention are vertically oriented, in contrast to the tops and bottoms of the invention. In the case of cupping and beveling of the top of the tablet, which may from time to time be extensive, the tablet's side is considered to also include the external part of the tablet that was in contact with the internal vertical face or aspect of the tablet die before a top punch formed said cupping, beveling, or the like.

If separate granulations were to be sequentially placed in a die horizontally (side-to-side) and not vertically as is currently the practice, then the tablets so produced would be within the scope of the present invention as the same product would be produced. When the tablet of FIG. 1, for example, is laid on a flat table, it will tend to lie lengthwise at right angles to the manner in which it is formed in the die (i.e., its longest axis would lie horizontally in relation to the tabletop), so that if the three segments were all different colors, then the segments would appear to be arranged not vertically (one on top of the other), but rather horizontally (side-to-side). For consistency of terminology, such segments nonetheless are considered herein to be disposed vertically on top of each other, because of the manner in which they were created.

One major advantage of the invention is that it optimizes optional tablet breaking. When force is applied to break a tablet, breaking of the tablet tends to more easily produce predictable quantities of active ingredient(s) in tablettes than "wider than tall" tablets with segments containing the same quantities of drugs. The tablet may be broken according to the invention either by applying force such as a cutting edge directly to the region to be broken through, or to outer segments, potentially in either case breaking through an inner segment.

Examples of specific embodiments of the invention are best described with reference to the drawings. Shaded areas represent segments derived from active granulations, i.e., those which contain a drug; clear (plain) areas represent segments derived from inactive granulations, i.e., those formulated with no active drug.

The drawings depict vertical cross-sectional views of tablets and tablettes of the invention. Tablets are depicted as if they were in the die, so that the top of the tablet as it is oriented on the page corresponds with the top of the tablet in the die. In other words, the top segment of the tablet as viewed contains the last granulation to enter the die. Tablettes are depicted as they would have been in the die before they were separated from the intact tablet.

"Front views" refer to a cross-sectional view of a tablet that has a theoretical geometric plane passed through the tablet relative to a side which is arbitrarily designated as the front. Figures labeled as "side view," which also have a corresponding "front view" are taken as a cross-section through the whole tablet from the right side of a front view i.e., a side view is a cross-section that is taken by passing a plane through the vertical axis of the whole tablet at a 90° angle to the cross-sectional front view. Each front view represents a schematic cross-section that passes through the midpoint of the horizontal cross-section as measured from the front of the tablet to the back of the tablet or tablette. The front view is also parallel to the major axis of the tablet (e.g., for a tablet with a rectangular (but not square) transverse cross-section, the longer side of the perimeter is parallel with the plane that depicts the cross-sectional, front view.

That plane is located half-way between the front and back surfaces of said tablet. The side views of FIGS. 1a-b and 2a-b are taken from a vertically-oriented plane that passes through the midpoint of the longer transverse dimension (i.e., the width), and thus are located at and perpendicular to the mid-point of the front view. Drawings are of tablets that have a rectangular but not square horizontal cross-section at the vertical mid-point of the tablet.

Segments containing pharmacologically active amounts of a drug or drugs are shown crosshatched; pharmacologically ineffective segments are shown plain (clear, without crosshatching or stippling). The upper part of each figure corresponds to the upper part of a tablet, all of which are depicted as they are situated within a die after final compression and before ejection from the die. For consistency, tablettes are depicted in the same orientation as the tablets from which they are formed, although tablettes are created after tablet ejection from the die. Dotted lines in the tablets depicted in the Figures may represent printed marks or other indicia, or scores that are present on or in the surface of the tablet and, if they represent a score, said score does not extend deeply enough into the tablet to appear in the cross-sectional front view. The transverse dotted lines reflecting scores shown in the Figures imply no intention to limit the depth of any scores of the tablets of the invention. Horizontal dotted lines on the front views that represent the surface scores are schematic, and do not necessarily represent the full vertical extent of a score, printed mark, or the like.

Tablettes are depicted with broken surfaces as indicated by a fine saw-tooth pattern. Such saw-tooth depiction is schematic and not intended to represent the actual pattern of breaking of a tablet (or tablette, which often leads to irregular edges even if said tablet is broken through a score.

Grasping and breaking said tablet is easier with the current, taller-than-wider design than would be the case under layered (segmented) tablets known to the art, in which breaking a tablet through one segment only, if feasible, would require "filleting" the tablet through its longest axis.

Figure 1A:
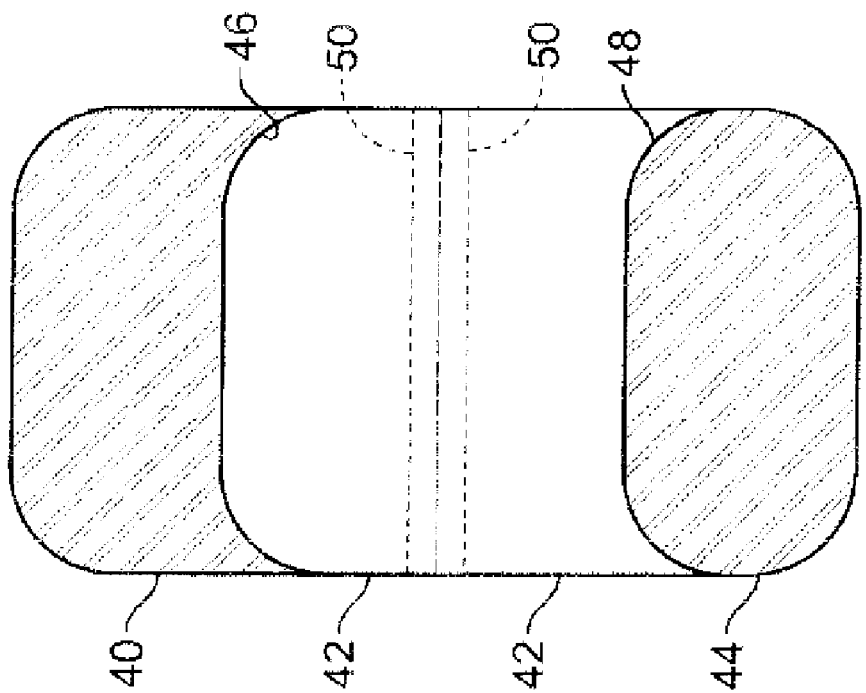
FIG. 1a is a cross-sectional view illustrating an embodiment of a taller than wide tablet of the subject invention, looking towards the side of the tablet having a score.
Figure 2C:
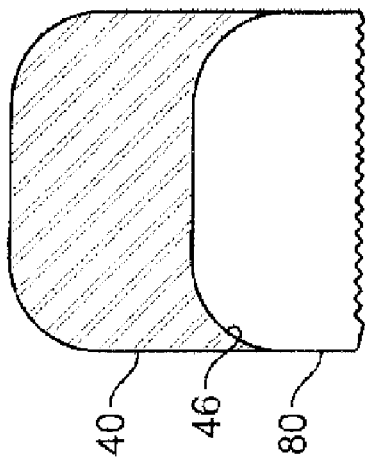
FIGS. 2a-d are views of FIG. 1a and FIG. 1b respectively when the tablets have been broken through the score.
Figure 2D:
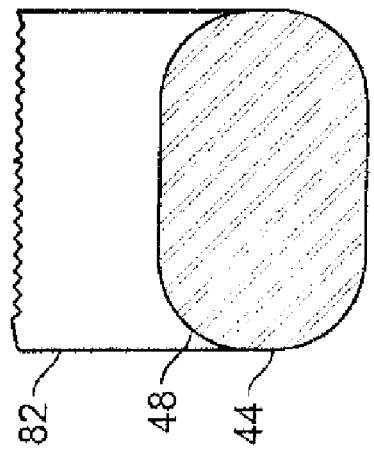
Figure 2A:
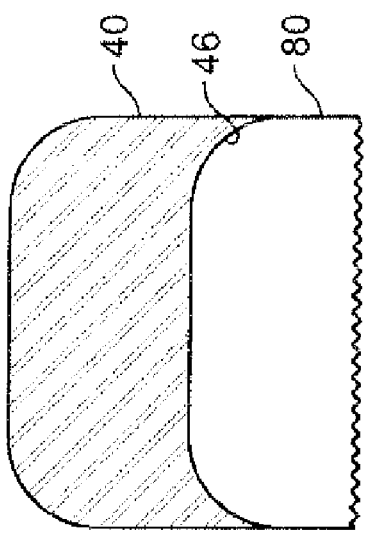
Figure 2B:
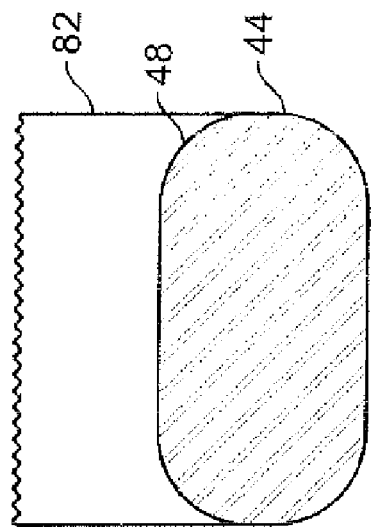

FIGS. 1a and 1b depict a tablet with compositionally substantially identical upper segment 40 and lower segment 44, both of which comprise at least one active ingredient, where the total active ingredient contained in both segments is a therapeutically effective amount of the drug. Inner segment 42 comprises a composition that is substantially free of active ingredient, but may contain, as an artifact of the manufacturing process, trace amounts of the drug that is present in a therapeutically effective quantity in each of segments 40 and 44. Interfaces 46 and 48 represent regions in which the upper part of segment 42 and the lower part of segment 42 respectively adjoin upper segment 40 and lower segment 44. The curved interfaces result from the profile of the upper tablet punch which is curved. Score 52 is depicted in FIG. 1b. Dotted line 50 in FIG. 1a is a reflection of score 52 on the surface of the tablet (not shown), that does not penetrate half-way through the shorter transverse axis of the tablet.

FIGS. 2a-d depict tablettes formed from breaking the tablet of FIGS. 1a and 1b through score 52. Inner segment 42 of FIG. 1a no longer exists as an intact segment. The upper tablette of FIGS. 1a and 1c contains segment 80 that adjoins intact upper segment 40 and the lower tablette contains segment 82 and intact segment 44.

Breaking the tablet of FIGS. 1a and 1b through the score placed in segment 42 is clearly easier than breaking the tablet through its vertical dimension, which is currently the practice with scored layered (segmented) tablets. The fact that no break is made in the parts of the tablet where the active drug has been placed provides for exceptionally accurate breaking relative to the active drug or drugs contained in the tablet.

Figure 3:
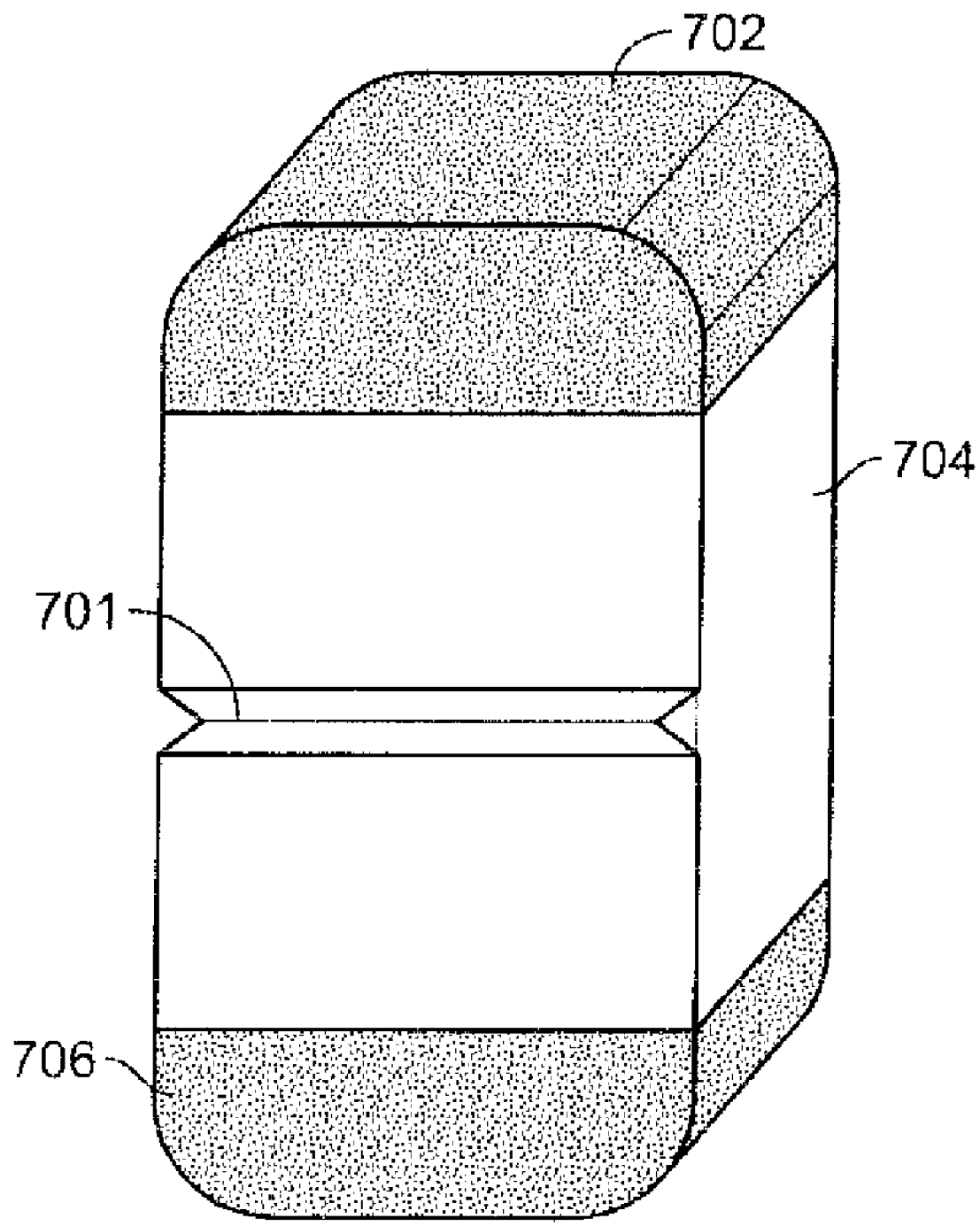
FIG. 3 is an external perspective view illustrating a scored tablet that has three segments.

FIG. 3 is a perspective view of a tablet of the invention which shows score 701 as a separating mark on a front surface and top active (drug-containing) segment 702; middle pharmacologically inactive segment 704 (no pharmacologically effective amount of a drug) and bottom active segment 706. When the tablet is broken through the score 701, the top segment and the bottom segment will remain intact. Segments 702 and 706 each contain a substantially identical compositions comprising at least one active pharmaceutical ingredient or drug.

Benefits of the invention are not limited to tablets of any specific number of active ingredients. All segments containing an active ingredient may contain the same drug, or segments may contain different drugs.

In order to fully realize the benefits of the invention, a score may be placed into a segment (or interface between segments) of the tablet. This score may be formed in an inner segment with a file in a substantially horizontal manner, so that breaking the tablet through said score could lead to breaking through the inner segment while leaving the outer segments intact.

In addition, similar means of marking tablets may be followed such as by causing an edible ink to be placed on the tablets, thus delineating a desired region of the tablet, such as its middle segment. Such application is well known in the art. Other means of applying indicia are contemplated as within the scope of the invention.

DESCRIPTION OF MANUFACTURING PREFERRED EMBODIMENTS

A "taller than wide" tablet is made which has three segments, each with an active top or upper segment and an active lower or bottom segment separated by a substantially inactive middle segment. A Stokes 27-station tri-layer rotary tablet press is used. All formulations are directly compressible powder blends. The blending both of the amlodipine formulation and the benazepril formulation are performed in a Patterson-Kelly "V" blender. The middle segment consists of 194 mg of Nu-Tab® and requires no blending. The tablets are compressed using 0.131 inch by 0.3222 inch oval, concave tablet punches to a hardness of 35 kilopounds. The bottom segment is introduced first into the die. The tablet weight is 310 mg. Tablets so made are 8 mm tall; the inactive middle segment varies from 5-6 mm in height and a width of 4 mm. Weights in mg of the granulation comprising each segment are as follow:

| Bottom Segment Ingredients | Mg. |
|---|---|
| Dibasic calcium phosphate anhydrous | 50.00 |
| Prednisone | 10.00 |
| Sodium starch glycolate (Explotab ®) | 2.50 |
| Magnesium stearate | 1.00 |
| FD&C Blue #1 Aluminum Lake | 0.50 |
| Total | 64.00 |

Manufacturing Instructions
1. Weigh each ingredient.
2. Screen each ingredient.
3. Triturate the color with the major diluent in geometric proportions using a suitable mixer.
4. Add the remaining ingredients, except the lubricant, to the color mixer from step #3 and mix for desired time.
5. Add the lubricant to the blend from Step #4 and mix for desired time.
6. Add the blend to a suitable press fitted with the desired tooling and compress into tablets.

| Middle Segment Ingredients | Mg. |
|---|---|
| Nu-Tab ® (Compressible sugar 30/35 N.F.) | 194.00 |

| Top Segment Ingredients | Mg. |
|---|---|
| Dibasic calcium phosphate anhydrous | 50.00 |
| Prednisone | 10.00 |
| Sodium starch glycolate (Explotab ®) | 2.50 |

-continued

| Top Segment Ingredients | Mg. |
|---|---|
| Magnesium stearate | 1.00 |
| FD&C Blue #1 Aluminum Lake | 0.50 |
| Total | 64.00 |

Manufacturing Instructions
1. Weigh each ingredient.
2. Screen each ingredient.
3. Triturate the color with the major diluent in geometric proportions using a suitable mixer.
4. Add the remaining ingredients, except the lubricant, to the color mixer from step #3 and mix for desired time.
5. Add the lubricant to the blend from Step #4 and mix for desired time.
6. Add the blend to a suitable press fitted with the desired tooling and compress into tablets.

Tabletting Instructions
1. Place the powder for active layer in hopper #1.
2. Place the powder for placebo layer in hopper #2.
3. Place the powder for active layer in hopper #3.
4. Compress layer #1 to desired weight (layer #1 should form a soft compact).
5. Compress layer #1 & Layer #2 to desired combined weight of layer #1 and layer #2 weight (layers should form a soft compact).
6. Compress layer #3 of the tri-layer tablet to the desired total tablet weight (layer #1 weight+layer #2 weight+layer #3 weight). This compression step can be used to compress the tablet to its desired hardness or can be used as a tamping step, followed by a further compression of the whole tablet to reach a desired hardness.

A similar tablet of the invention is separately produced using the same top and bottom segments as the above, but using the following ingredients instead of Nu-Tab for the middle segment. The following are blended using a Patterson-Kelly "V" blender.

| Ingredients for middle segment: | Mg. |
|---|---|
| Dibasic calcium phosphate anhydrous | 158.59 |
| Magnesium stearate | 2.79 |
| PVP K-30 | 2.62 |
| Total | 164.00 |

Manufacturing Instructions
1. Weigh each ingredient.
2. Screen each ingredient.
3. Place all of the ingredients, except the lubricant, into a suitable mixer and mix for desired time.
4. Add the lubricant to the blend from Step #3 and mix for desired time.
5. Add the blend to a suitable press fitted with the desired tooling and compress into tablets.

The tablets were compressed using oval 0.131 inch by 0.3222 inch, concave tablet punches to a hardness of 35 kilopounds. The bottom segment was introduced first into the die. The tablet weight was between about 300-350 mg. Tablets with said middle segment were 6 mm high, and the inactive middle segment was 3.5-4 mm high.

Tabletting Instructions
1. Place the powder for active layer in hopper #1.
2. Place the powder for placebo layer in hopper #2.
3. Place the powder for active layer in hopper #3.
4. Compress layer #1 tablets to desired weight (tablets for layer #1 should form a soft compact).
5. Compress layer #1 & Layer #2 tablets to desired combined weight of layer #1 and layer #2 weight (tablets should form a soft compact).
6. Compress the tri-layer tablet to the desired total tablet weight (layer #1 weight+layer #2 weight+layer #3 weight) Tablet should be at desired hardness.

In a similar way, other taller than wide tablets can be made on a tablet press, such as, the Korsch TRP900 which can produce taller tablets due to its design for deep filling cams which allow for deeper fills and greater distances between the upper and lower compression tools.

To make an oval 0.131 inch by 0.3222 inch, concave tablet that is 12 mm tall on the Korsch TRP900 the formulator would have to increase the weight of the inactive Nu-Tab® middle segment to about 323 mg. Similarly to have a finished tablet height of 14 mm the tablet would be formulated with a middle segment weighing about 388 mg. If the formulator preferred, they could use the second example for a middle layer, i.e., the dibasic calcium phosphate (DCP) formulation. In such a case making an oval 0.131 inch by 0.3222 inch, concave tablet that is 12 mm tall on the Korsch TRP900 the formulator would have to increase the weight of the inactive DCP middle segment to about 410 mg. Similarly to have a finished tablet height of 14 mm the tablet would be formulated with a middle segment weighing about 492 mg.

The invention also includes the method of administering one or more drugs via the dosage forms such as tablets and tablettes of the invention to a patient, mammal, or other animal in need of pharmaceuticals for the prevention or treatment of an illness, maintenance of good health, retarding of aging, or other purpose. Included are methods of treating a patient with only one tablette of the invention, enabling downward dose adjustment for a variety of reasons; or, in a similar vein, a patient may be treated with one whole tablet containing active drug and in addition receive a tablette from a similar tablet, thus enabling upward dose adjustment. Active pharmaceutical ingredients used in a tablet of the subject invention can preferably include warfarin, a statin, risperidone, methotrexate, metformin, atenolol, prednisone, phenytoin, lamotrigine, or meloxicam used as the sole active pharmaceutical ingredient or in combination with another active pharmaceutical ingredient. Combination products that can benefit from the invention, in which more than one drug is in the outer active segments, include those containing the following pairs of drugs: amlodipine and either benazepril, chlorthalidone, or atorvastatin; benazepril and hydrochlorothiazide; olmesartan and hydrochlorothiazide; and many others, including the majority of the currently-produced combination products. Also included is the method of treating a patient with a precise partial close of medication from a whole tablet, which may be a half or quarter of the whole dose, but may usefully be a different fraction. Warfarin especially may usefully be produced and dosed according to the invention with separable segments of the tablet that may but need not be as halves, quarters, etc. L-thyroxine and digoxin are other examples that could so benefit, along with warfarin.

The following list of possible combinations of a plurality of drugs is exemplary and not limiting. The combinations referred to may include two or more members of the classes listed. Drugs listed below, and herein, may for convenience exclude mention of any salt of a drug; e.g., "atorvastatin" is listed even though its marketed form is atorvastatin calcium.

Without limitation, useful combinations may include a plurality of drug from within the following six drug classes. In addition, tablets of the invention may be created containing only one of a drug from the following list. With regards to combination use, one method is to place a plurality of drugs in both end segments.

1. Anti-anginal agents, for example:
   A. Calcium antagonists (see list below);
   B. Beta-blocker (see list below);
   C. Organic nitrate preparation (e.g., isosorbide mononitrate or dinitrate).
2. Anti-anginal agent plus an anti-platelet agent, such as aspirin, clopidogrel, or ticlopidine.
3. Two hypoglycemic agents (see list below).
4. Potassium chloride and any thiazide-type or loop diuretic (see lists below).
5. Lipid-lowering agent plus: hypoglycemic agent, anti-platelet agent, anti-anginal agent, and/or antihypertensive agent (see lists above and below)
   Hypoglycemic agents include: thiazolidinediones: pioglitazone, rosiglitazone; sulfonylureas: glyburide, glipizide, glimepiride, chlorpropamide;
   Biguanides: metformin;
   Meglitinides: nateglinide, repaglinide;
   Glucosidase inhibitors: acarbose, miglitol.
6. Antihypertensive agents:
   Beta-blockers: acebutolol, atenolol, bisoprolol, celiprolol, metoprolol, mebivolol, carvedilol (a mixed alpha-beta blocker), nadolol, oxprenolol, penbutolol, pindolol, propranolol, timolol, betaxolol, carteolol;
   Calcium antagonists (calcium-channel blockers): nifedipine, amlodipine, verapamil, diltiazem, nisoldipine, felodipine, isradipine, lacidipine, lercanidipine, nicardipine, manidipine;
   Thiazide-type diuretics (with or without potassium-retaining diuretics such as triamterene, amiloride, or spironolactone): hydrochlorothiazide, chlorothiazide, cyclopenthiazide, polythiazide, bendrofluazide, hydroflumethiazide, chlorthalidone, indapamide, methylclothiazide, metolazone;
   Angiotensin converting enzyme inhibitors: captopril, enalapril, lisinopril, ramipril, trandolapril, quinapril, perindopril, moexipril, benazepril, fosinopril;
   Angiotensin receptor blockers: losartan, valsartan, candesartan, telmisartan, eprosartan, irbesartan;
   High-ceiling (loop) diuretics (with or without potassium-retaining diuretics such as triamterene, amiloride, or spironolactone): furosemide, torsemide, ethacrynic acid, bumetamide;
   Aldosterone antagonist diuretics: spironolactone, eplerenone;
   Alpha-blockers: doxazosin, terazosin, prazosin, indoramin, labetolol (a mixed alpha-beta blocker);
   Central alpha-agonists: clonidine, methyldopa;
   Imidazoline: moxonidine;
   Direct vasodilators: hydralazine, minoxidil;
   Adrenergic neuronal blocker: guanethidine.
   Lipid-lowering agents include:
   Statins: lovastatin, simvastatin, pravastatin, rosuvastatin, atorvastatin, fluvastatin;
   Fibrates: clofibrate, bezafibrate, fenofibrate, gemfibrozil, ciprofibrate;
   Others: ezetimide, niacin, acipimox.

The drugs used as a monotherapy or the combinations of drugs disclosed herein are for illustrative purposes and are not intended to limit the scope of the invention. Preferred embodiments include tablets comprising warfarin, a statin, risperidone, methotrexate, metformin, atenolol, prednisone, phenytoin, lamotrigine, or meloxicam as the active pharmaceutical ingredient in a divisible tablet of the subject invention.

Regarding the important usage of the tablets and tablettes of the invention, that involving division of a tablet into tablettes containing similar active segments, most drugs that may undergo dosage adjustment will be preferred if they may be divided in an optimally precise manner. Examples of drugs that will especially benefit from the advances of the invention in this manner include narrow therapeutic index drugs such as warfarin, digoxin, L-thyroxine; vasoactive drugs such as amlodipine; hypoglycemic agents such as rosiglitazone and glipizide; and anxiolytics drugs such as alprazolam. These are however but a small fraction of the great mass of drugs that will benefit from the various embodiments and procedures of the invention.

There are numerous methods of use of the dosage forms of the invention, including its tablets and tablettes. Persons skilled in the medical and pharmaceutical arts will recognize the many advantages that the various embodiments of the invention allow over current products. Some examples of benefits of the inventions involving tablets containing exactly one similar active segment are described immediately below.

1. Warfarin is an anticoagulant marketed in the U.S. under the brand name Coumadin®, which is a scored tablet. Research has shown that patients do not break warfarin 5 mg tablets into equal 2.5 mg segments. The invention teaches different types of tablets that allow warfarin tablets of any common human dose to be broken into precise halves, and potentially precise thirds, quarters, etc. Thus a patient may utilize warfarin half-tablets produced as per the invention with similar confidence as in the whole tablet. Because warfarin doses are frequently broken, many clinical scenarios exist in which the invention will benefit patients.
2. Norvasc® (amlodipine besylate or amlodipine herein) is marketed as unscored 2.5, 5, and 10 mg tablets in the U.S. These tablets are of irregular shape and are difficult to break. The FDA-approved dosage range is from 2.5 to 10 mg ingested orally daily. The invention allows improved functionality of amlodipine. For example, under the invention, a patient receiving 5 mg daily who a physician wishes to increase to 7.5 mg daily may simply utilize a tablet of the invention that comprises two separate 2.5 mg segments to increase the dose to precisely 7.5 mg, such as by ingesting one whole 5 mg tablet and one 2.5 mg tablette created by breaking a 5 mg tablet into two tablettes each containing 2.5 mg of amlodipine. Convenience and cost savings are clear. Similarly, a patient receiving a 10 mg dose of Norvasc who is advised to reduce the dose to 5 mg daily must currently purchase a new prescription for 5 mg Norvasc tablets. The invention provides the ability to provide a 10 mg tablet that may be broken into two tablettes, each containing precisely 5 mg of amlodipine. The invention may therefore enable greater flexibility of treating patients, and provide cost savings as well.

A further benefit of the invention may relate to pediatric or geriatric doses, which may not be produced in appropriate dose strengths. In the case of amlodipine, a 1.25 mg daily dose may be useful in either small children with hypertension, or in frail elderly patients with angina or hypertension, who may have hepatic dysfunction. Even though the United States Food and Drug Administration (FDA) has not approved a 1.25 mg dose, precise divisibility of the approved 2.5 mg dose would allow a 1.25 mg daily dose. In addition, precise divisibility of the approved 2.5 mg dose will allow accurate dosing of 3.75 mg daily.

Another use of the invention is to for the first time enable a method of cost savings to insurers and patients. The invention allows this because many drugs, such as Norvasc and Coumadin, have pricing that differs little (if at all) between different doses. Because tablet splitting is imprecise for most scored tablets, the practice of mandatory splitting has been met with disapproval by most physician and pharmacist organizations. The invention enables tablet splitting due to provide accurate dosing when a tablet of the invention are broken as described herein. Substantial benefits are foreseen from this innovation. In addition, the ability to separate one active drug from another in a combination product has cost saving advantages, as well.

It is recognized that related inventions may be within the spirit of the disclosures herein. Also no omission in the current application is intended to limit the inventors to the current claims or disclosures. As this application is a continuation-in-part of pending U.S. patent application Ser. Nos. 11/569,343; 10/598,267; and 10/598,306, each of which claims priority to U.S. Provisional Appl'n Ser. No. 60/573,042 filed May 21, 2004 and U.S. Provisional Appl'n Ser. No. 60/573,134 filed May 21, 2004, these applications are hereby incorporated by reference in their entirety as applicable. While certain preferred and alternative embodiments of the invention have been set forth for purposes of disclosing the invention, modifications to the disclosed embodiments may occur to those who are skilled in the art.

We claim:

1. A compressed, immediate-release pharmaceutical tablet containing a therapeutic dose of one or more active pharmaceutical ingredients and having a greater height than width, said height being measured vertically from the top to the bottom of said tablet while it is in the tablet die in which it is fully compressed, after said compression has been completed; and said width being measured as the greatest horizontal dimension of the tablet at a location halfway between said top and said bottom of said tablet, except that when the horizontal cross-section of said tablet is substantially rectangular, the width is defined by locating the two shorter sides of the perimeter of said horizontal cross-section, and measuring the length of a line that is at right angle to said shorter sides, said tablet consisting essentially of:

a bottom end segment comprising an immediate-release composition containing at least about half of said therapeutic dose of the one or more active pharmaceutical ingredient, said bottom end segment having an exposed bottom end and a contacting face opposite its exposed bottom end;

a top end segment comprising a composition substantially identical to the composition of said bottom end segment, said top end segment having an exposed top end and a contacting face opposite its exposed top end;

a middle segment located between said bottom end segment and said top end segment, said middle segment comprising a composition consisting essentially of immediate-release excipients and being substantially free of active pharmaceutical ingredient, said middle segment having a bottom face in contact with the contacting face of said bottom end segment, a top face in contact with the contacting face of said top end segment, and an exposed outer side surface; and optionally, an immediate-release coating substantially free of active pharmaceutical ingredient.

2. The tablet of claim 1 wherein said outer side surface of the middle segment comprises a substantially horizontal score transverse to the vertical axis of the tablet.

3. The tablet of claim 1 wherein the score is positioned such that a plane passing through the score substantially bisects the tablet.

4. The tablet of claim 1 wherein the score is positioned such that a plane passing through the score substantially bisects the height or effective height of the middle segment.

5. The tablet of claim 1 wherein the tablet is uncoated.

6. The tablet of claim 1 wherein said tablet is coated, said coating comprising a water-soluble polymer.

7. The compressed pharmaceutical tablet of claim 1 wherein the bottom end segment comprises an active pharmaceutical ingredient selected from the group consisting of warfarin, a statin, risperidone, methotrexate, metformin, atenolol, prednisone, phenytoin, lamotrigine, and meloxicam.

8. The compressed pharmaceutical tablet of claim 1 wherein the bottom end segment comprises warfarin.

9. The compressed pharmaceutical tablet of claim 1 wherein the bottom end segment comprises a statin.

10. The compressed pharmaceutical tablet of claim 1 wherein the bottom end segment comprises methotrexate.

11. The compressed pharmaceutical tablet of claim 1 wherein the bottom end segment comprises metformin.

12. The compressed pharmaceutical tablet of claim 1 wherein the bottom end segment comprises atenolol.

13. The compressed pharmaceutical tablet of claim 1 wherein the bottom end segment comprises phenytoin.

14. The compressed pharmaceutical tablet of claim 1 wherein the bottom end segment comprises lamotrigine.

15. A compressed, immediate-release pharmaceutical tablet containing a therapeutic dose of one or more active pharmaceutical ingredients and having a greater height than width, said height being measured vertically from the top to the bottom of said tablet while it is in the tablet die in which it is fully compressed, after said compression has been completed; and said width being measured as the greatest horizontal dimension of the tablet at a location halfway between said top and said bottom of said tablet, except that when the horizontal cross-section of said tablet is substantially rectangular, the width is defined by locating the two shorter sides of the perimeter of said horizontal cross-section, and measuring the length of a line that is at right angle to said shorter sides, said tablet consisting essentially of:

a bottom end segment comprising an immediate-release composition containing at least about half of said therapeutic dose of the one or more active pharmaceutical ingredient, said bottom end segment having an exposed bottom end and a contacting face opposite its exposed bottom end;

a top end segment comprising a composition substantially identical to the composition of said bottom end segment, said top end segment having an exposed top end and a contacting face opposite its exposed top end;

a middle segment located between said bottom end segment and said top end segment, said middle segment comprising a composition consisting essentially of immediate-release excipients and being substantially free of active pharmaceutical ingredient, said middle segment having a bottom face in contact with the contacting face of said bottom end segment, a top face in contact with the contacting face of said top end segment, and an exposed outer side surface, said outer side surface comprising a substantially horizontal score positioned such that a plane passing through said score substantially bisects the tablet or middle segment; and optionally, an immediate-release coating substantially free of active pharmaceutical ingredient.

16. The tablet of claim 15 wherein said score is positioned such that a plane passing through said score substantially bisects the height of the middle segment.

17. The tablet of claim 15 wherein said score is positioned such that a plane passing through said score substantially bisects the effective height of the middle segment.

18. The tablet of claim 15 wherein said tablet is uncoated.

19. The tablet of claim 14 wherein said tablet is coated, said coating comprising a water-soluble polymer.

20. A compressed, immediate-release pharmaceutical tablet containing a therapeutic dose of one or more active pharmaceutical ingredients and having a greater height than width, said height being measured vertically from the top to the bottom of said tablet while it is in the tablet die in which it is fully compressed after said compression has been completed; and said width being measured as the greatest horizontal dimension of the tablet at a location halfway between said top and said bottom of said tablet, except that when the horizontal cross-section of said tablet is substantially rectangular, the width is defined by locating the two shorter sides of the perimeter of said horizontal cross-section, and measuring the length of a line that is at right angle to said shorter sides, said tablet consisting essentially of:

a bottom end segment comprising an immediate-release composition containing at least about half of said therapeutic dose of the one or more active pharmaceutical ingredient, said bottom end segment having an exposed bottom end and a contacting face opposite its exposed bottom end;

a top end segment comprising a composition substantially identical to the composition of said bottom end segment, said top end segment having an exposed top end and a contacting face opposite its exposed top end;

a middle segment located between said bottom end segment and said top end segment, said middle segment comprising a composition consisting essentially of immediate-release excipients and being substantially free of active pharmaceutical ingredient, said middle segment having a bottom face in contact with the contacting face of said bottom end segment, a top face in contact with the contacting face of said top end segment and an exposed outer side surface, said outer side surface comprising printed indicia positioned substantially horizontally such that a plane passing through said printed indicia substantially bisects the tablet or middle segment; and optionally, an immediate-release coating substantially free of active pharmaceutical ingredient.

\* \* \* \* \*